United States Patent [19]

Tanguy

[11] Patent Number: 5,525,772
[45] Date of Patent: Jun. 11, 1996

[54] INSTANT NEEDLE SYRINGE DESTROYER

[75] Inventor: Pierre Tanguy, Courbevoie, France

[73] Assignee: The Andrus Corporation, San Francisco, Calif.

[21] Appl. No.: 265,313

[22] Filed: Jun. 23, 1994

[51] Int. Cl.$^6$ .................................................. B23K 11/22
[52] U.S. Cl. .................................................. 219/68
[58] Field of Search ........................ 219/68; 320/48

[56] References Cited

U.S. PATENT DOCUMENTS

| | | | |
|---|---|---|---|
| 4,027,231 | 5/1977 | Lohrmann | 320/48 |
| 4,396,881 | 8/1983 | Cook et al. | 320/48 |
| 4,965,426 | 10/1990 | Colombo | 219/68 |
| 5,105,180 | 4/1992 | Yamada et al. | 320/48 |
| 5,144,218 | 9/1992 | Bosscha | 320/48 |
| 5,212,362 | 5/1993 | Burden et al. | 219/68 |
| 5,264,675 | 11/1993 | Butler | 219/68 |
| 5,294,767 | 3/1994 | Cantarero | 219/68 |
| 5,412,307 | 5/1995 | Yoshimatsu | 320/48 |
| 5,468,928 | 11/1995 | Yelvington | 219/68 |

*Primary Examiner*—Geoffrey S. Evans
*Attorney, Agent, or Firm*—Benman Collins & Sawyer

[57] ABSTRACT

A portable needle syringe destroyer apparatus that includes a housing with a handle, three lights and a switch on top and a metal plate on, the front at an oblique angle. The destroyer apparatus includes: a battery, battery charge monitor, battery charger and current regulator interior to the housing. The metal plate floats on a spring and moves when a needle is inserted into the opening on the plate. The current is applied through the switch to instantly heat the metal plate high enough and cause the immediate destruction of the needle, any pathogens on or in it and seal the syringe with a small metal ball at the needle hub. The result is irrevocably disposing of the needle and rendering their toxins harmless.

11 Claims, 7 Drawing Sheets

INSTANT NEEDLE SYRINGE DESTROYER

FIELD OF THE INVENTION

The present invention relates generally to an apparatus for disposing of needles utilized for medical purposes, more particularly to the destruction of such needles after use.

BACKGROUND OF THE INVENTION

The growth and spread of blood borne diseases, notably Hepatitis B and the HIV virus, in the United States and throughout the world has reached crisis proportions. Methods must be developed to combat this growth.

Medical use of needles in syringes, IV's and blood withdrawal result in the need for safe disposal of the needles after use. Blood borne pathogens such as Hepatitis B and HIV/AIDS, can contaminate a used needle. When an injection is given, the blood of the recipient is left on the exterior of the needle and can also enter the tip of the needle, sometimes flowing all the way to the syringe, thus infecting all or part of the device. Withdrawal of blood for tests and blood banks involve drawing potentially infected blood into the needle and syringe area.

There are many locations where needles are used: hospitals, nursing care facilities, doctor's offices, ambulances, MASH units, mobile health care units, emergency hospitals, clinics, etc. as well as private home use by diabetics and others requiring injections and IV's.

Other uses of needles such as research and laboratory use, Veterinarian use and tattooing also results in the creation of a potentially infected waste product.

The infected needle products must be disposed of safely so that they do not infect medical personnel or the public and so that they are not reusable and thus able to infect other persons or animals. The infected needle products must be disposed of safely so that they do not infect medical personnel or the public and so that they are not reusable and thus able to infect other persons or animals.

The present systems of disposal involve mandatory use of a special waste canister or "red box" where the used needles are placed awaiting transport to a disposal facility. The facility must incinerate the "red box" so that the needles cannot be reused or re-infect. Sometimes large red plastic bags are used to contain re-capped needles in comprehensive inoculation programs.

Some disposable needle syringes are capable of being broken to avoid re-use, but still remain toxic. Processes exist for crushing, cutting or grinding the needle. However no matter how sophisticated the method is, the needles may still be toxic and thus dangerous.

Risk, liability and insurance is high at all points on the needle's trip to incineration:

At the use site: a puncture could occur during the capping of the used needle after use; accidents are possible when disposing the used needles into the "red box" or bag; and primarily, the used needles are not treated in any way and remain toxic in the canister or bag. The canister is sometimes left unattended in the use site or patient's private home.

In transit: accidents are always possible in transit. Currently private parties that must use needles at home may send them to a waste disposal site in special containers through the US Mail.

At the waste disposal site: handling errors may occur. Incineration must be total to be effective.

All current systems still depend upon proper disposal of the canister by third party disposal companies. There have been several incidents of needles, supposed to be properly handled, turning up on beaches and in other public places. All current systems depend upon ultimately transporting potentially toxic objects possessing the ability to prick the flesh.

What is needed, therefore, is a system for the disposal of needles that overcomes the above mentioned problems. More particularly, the system should be such that the pathogens on needles can be effectively destroyed at the site before transport. The apparatus should be portable, simple and cost effective. The present invention addresses such a need.

SUMMARY OF THE INVENTION

The present invention is directed toward a portable apparatus that achieves the destruction (about one second in duration) of a hypodermic needle using high temperatures (between 1100° and 1300° C.) that is generated by an electrical current. In a preferred embodiment, the end of the needle is heated to 300° C., thereby also decontaminating the needle.

The apparatus utilizes an electrical circuit that provides the following functions:

a current that produces intense and the sudden heat to the metal plate of the device.

monitors a battery and disables the circuit at the conclusion of its discharge during use, and provides for an automatic shut off when not in use.

Through the application of heat, by an electrical circuit, to a metal plate a needle when brought in contact with the plate will provide for the destruction of the needle, except for the metal residue of the needle. In addition, by the sterilization of any pathogens contained within or upon the metal object—the needle.

DETAILED DESCRIPTION

The present invention relates to a apparatus for destroying needles. The following description is presented to enable one of ordinary skill in the art to make and use the invention as provided in the context of a particular application and its requirements. Various modifications to the preferred embodiment will be readily apparent to those skilled in the art, and the generic principles defined here may be applied to other embodiments. Thus, the present invention is not intended to be limited to the embodiments shown, but is to be accorded the widest scope consistent with the principles and novel features disclosed herein.

Figure 1:
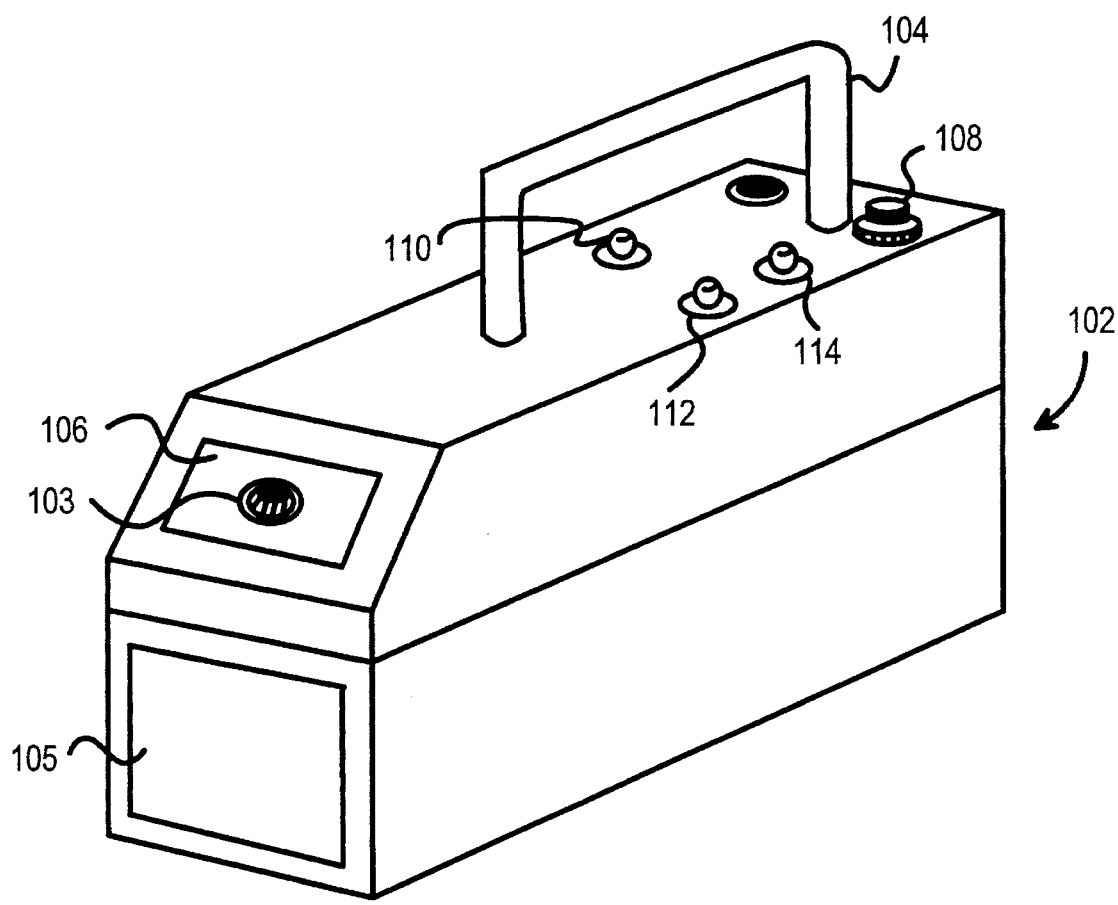
FIG. 1 is a first perspective view of the needle syringe destroyer apparatus in accordance with the present invention.
Figure 2:
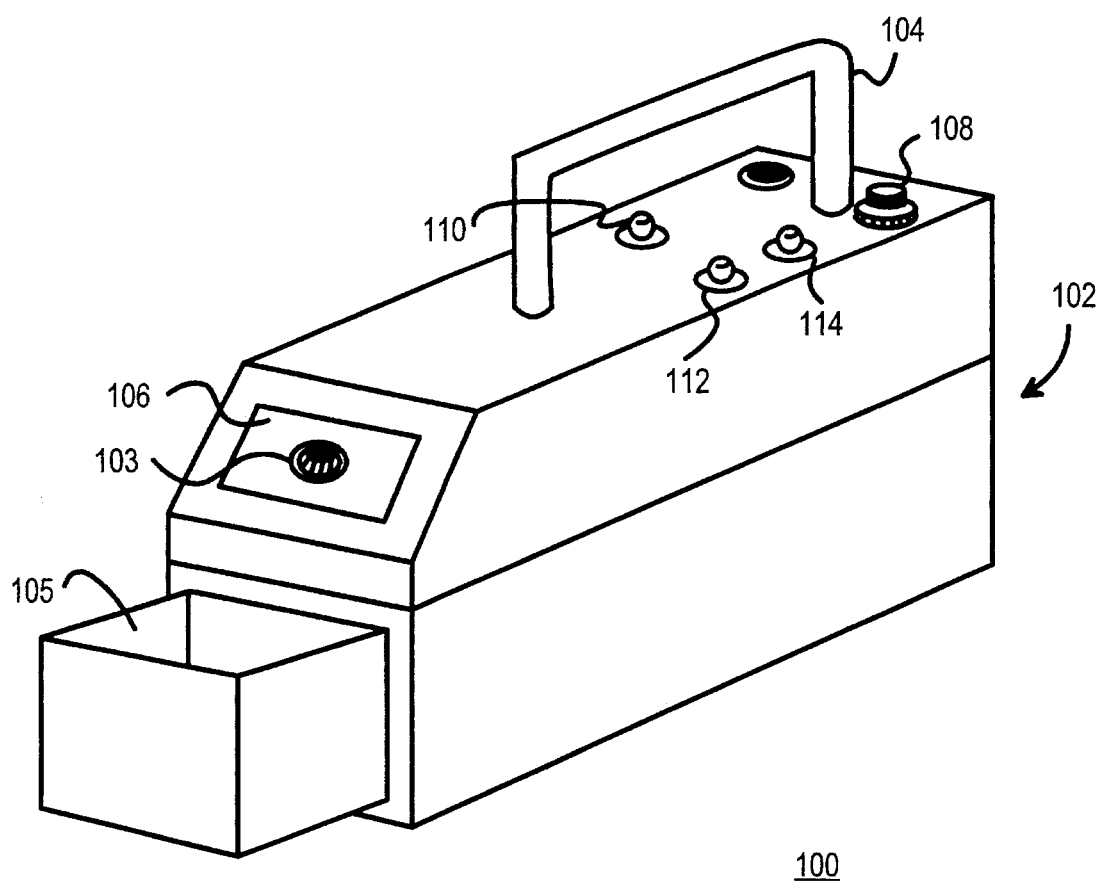
FIG. 2 is a second perspective view of the needle syringe destroyer apparatus in accordance with the present invention.
Figure 3:
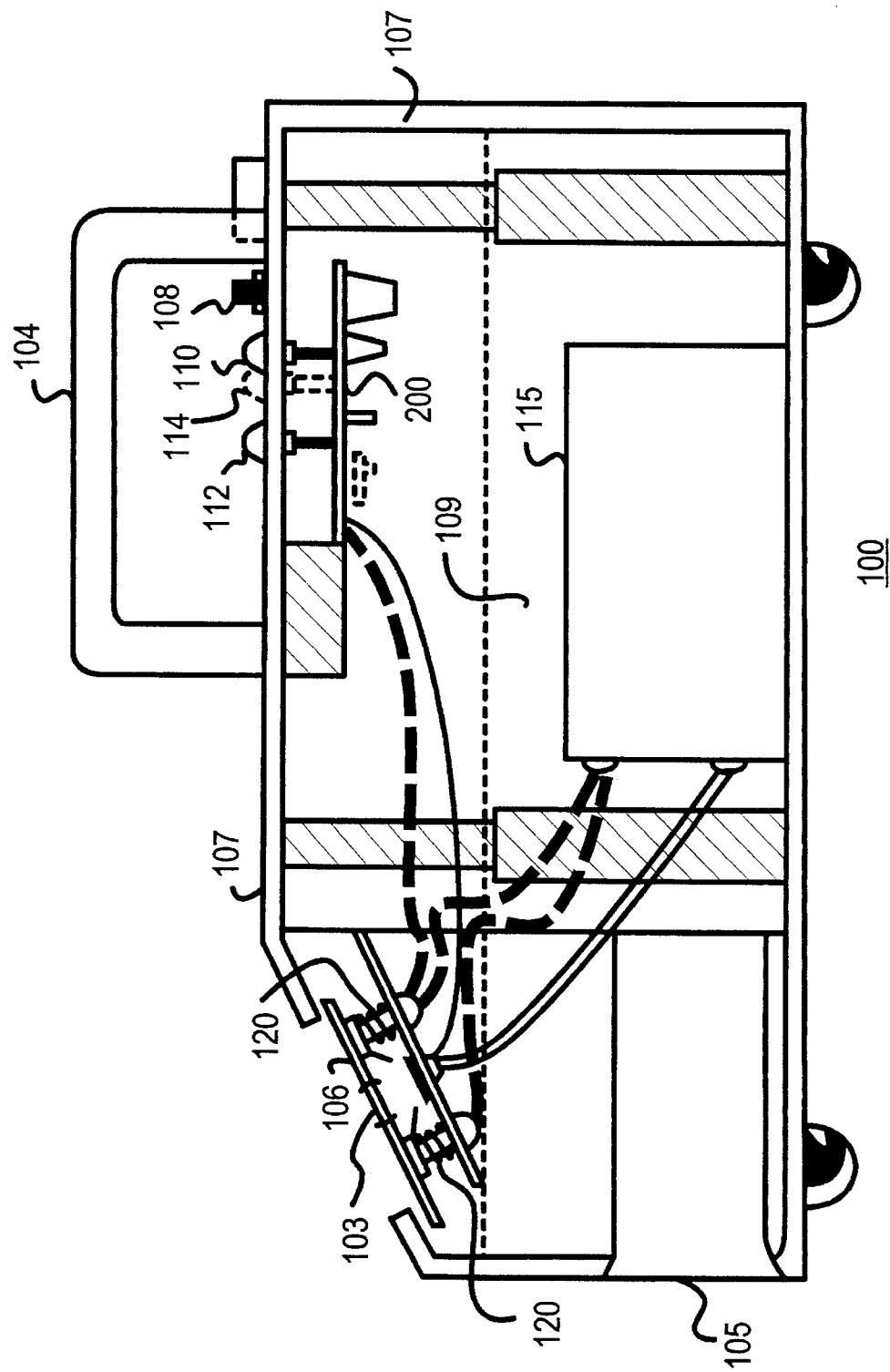
FIG. 3 is a cutaway view of the destroyer apparatus of FIG. 1.

Referring now to FIGS. 1, 2 and 3 which shows first and second perspective views and a cutaway view of the needle syringe destroyer apparatus 100. In a preferred embodiment, the destroyer apparatus 100 comprises a housing 102. The housing 102 includes a handle 104 coupled to an exterior portion 107 for transporting the apparatus 100. A metal plate 106 which is in this embodiment at the oblique angle in the front of the housing 102 includes an opening 103. The plate 106 is also movable a short distance via springs 120. A drawer 105 is located beneath the metal plate 106 to retain the metal residue when a needle is melted by the apparatus 100. As is seen in FIG. 2 the drawer 105 is removable from the apparatus 100 to allow for easy disposal of the residue.

Also on the exterior portion 107 of the housing 102 is a switch 108 and three lights 110, 112 and 114 which are red, green and amber, respectively. Also included to an interior portion 109 of the housing 102 is an electrical circuit 200 and a battery 115. The circuit 200 is coupled to the metal plate 106, the lights 108, 110, and 112 and the battery 115.

The circuit 200 in cooperation with the battery 115 supplies the current to the metal plate 106. The current, in turn generates the heat necessary to disintegrate a needle which is part of a hypodermic syringe. The circuit 200 then turns itself off after use. Accordingly, in a preferred embodiment, the user does not have to regulate the temperature or turn off the power to the destroyer apparatus 100 after use.

Figure 4:
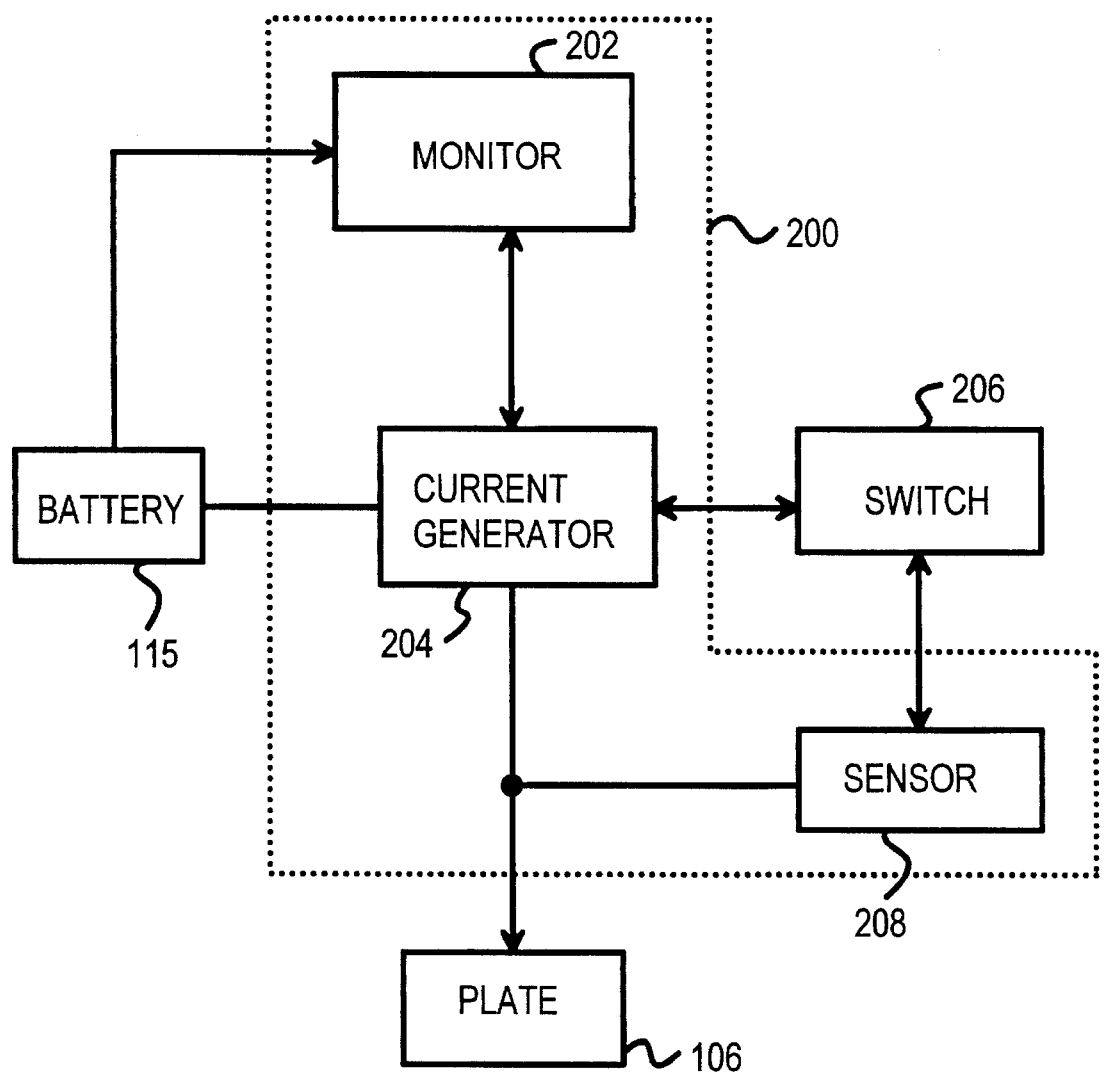
FIG. 4 is a block diagram of the operation of the circuit utilized in the needle syringe destroyer of FIG. 1.

To more particularly describe the operation of the electrical circuit 200, refer now to FIG. 4 which is a block diagram of the electrical circuit 200 utilized in destroyer apparatus 100. The circuit 200 comprises a battery monitor 202 which is coupled to the battery 115. The battery monitor 202 provides an indication of the voltage level of the battery 115. A current generator 204 is coupled to the battery monitor 202 and the battery 115 to provide current to the metal plate 106.

The switch 108 activates the current generator 204 so as to provide current to plate 106. The plate 106, as before mentioned, will melt a needle that comes into contact with the plate 106. A sensor 208 coupled between the switch and an output of the current generator 204 is utilized to control the switch 108 such that the switch 108 will shut off the circuit 200 after a predetermined time period.

Figure 5:
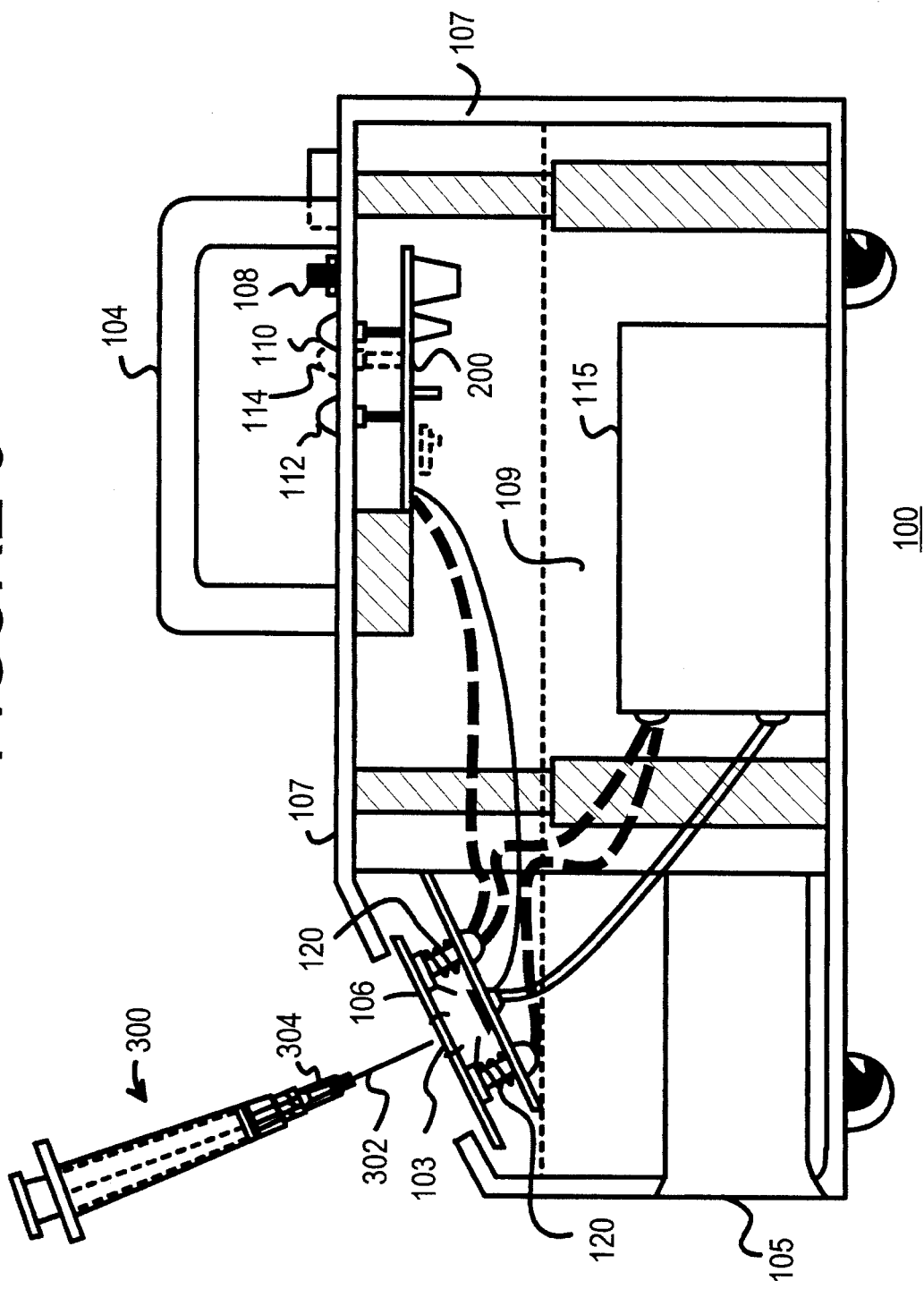
FIG. 5 is a view of the needle syringe destroyer apparatus of FIG. 1 just before a needle is inserted in an opening.
Figure 6:
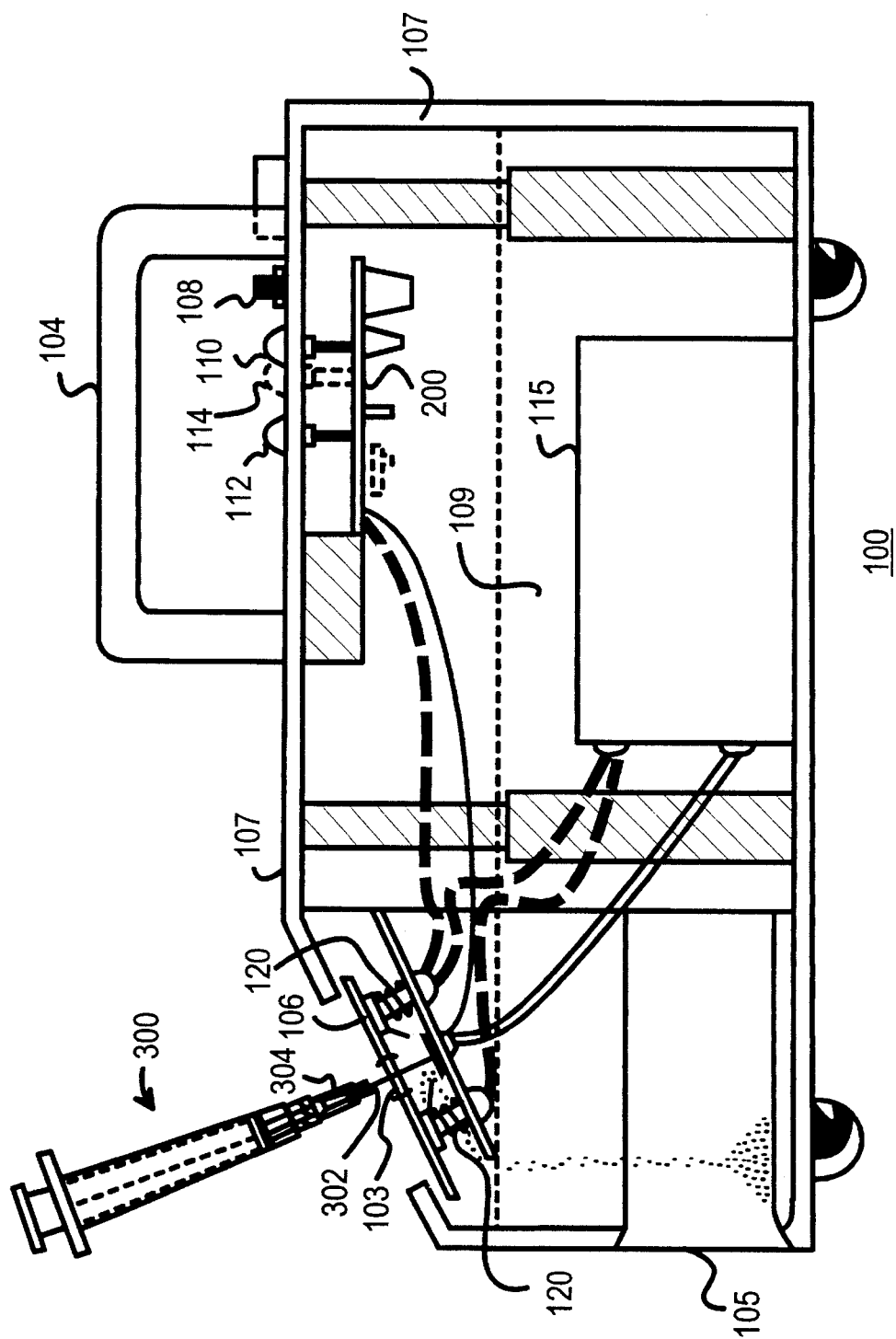
FIG. 6 is a view of the destroyer apparatus of FIG. 1 while the needle is inserted in the opening.
Figure 7:
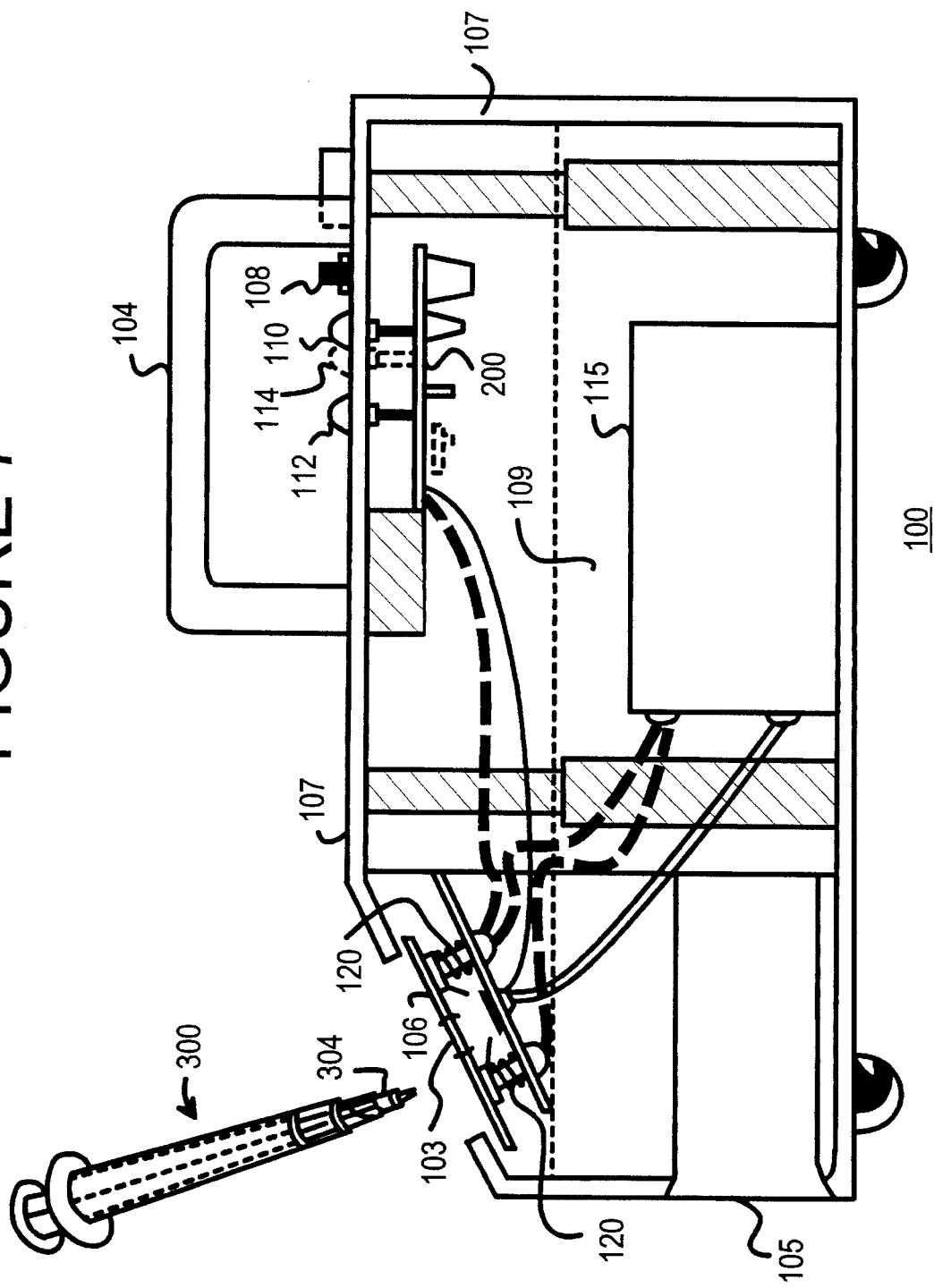
FIG. 7 is a view of the destroyer apparatus of FIG. 1 after the needle is removed from the opening.

To more fully understand the operation of the apparatus 100 refer now to FIGS. 5-7 and the following. FIGS. 5-7 show the operation of the apparatus 100, just before a needle 300 is inserted, while the needle 300 is inserted and after the needle 300 removed from the apparatus 100, respectively.

Operation

Referring first to FIG. 5, to turn on the apparatus 100, the switch 108 is depressed. If the green light 112 becomes active indicating that the battery 115 is sufficiently charged, that is an indication that the destruction of the needle 302 of the syringe 300 can commence. If, instead, the red light 110 becomes active after the switch 108 is depressed, the battery 115 must be recharged. At the end of recharging, the amber light 114 will blink, signaling that battery 115 is sufficiently recharged for use.

The user (not shown) should be able to hold the apparatus 100 with one hand, by the handle 104 (situated so as to avoid the risk of needle prick through any slip or faulty movement by the hand holding the needle). The other hand firmly holds the syringe 300 and drives the needle into the opening 116 located in the middle of the plate 103 on the front of the destroyer apparatus 100 (FIG. 5). The plate 106 is placed at an oblique angle to give the optimum view, convenience of use and personal security.

A simple moderate pressure of a second in duration on the needle causes the needle to "melt" and "disappear" (in the preferred embodiment, the maximum destruction time is 10 seconds): the residue, not visible to the user, will have fallen as residue in the drawer 105. The needle 302 of the syringe 300 has been destroyed up to its plastic guard 304 and the opening to the syringe 300 is sealed (FIG. 6). The apparatus, therefore, through this process will seal the syringe 300 at the plastic guard 302 with a melted metal ball, thus preventing any possible pathogens or drugs inside the syringe 300 from escaping. The syringe 300 is then safe for transport to the disposal site.

Referring back to FIG. 3, the shape of the opening 103 of the plate 106, and the fact that the plate 106 is movable and floats on springs 120 (as the needle 302 is pushed down, the plate 106 moves with it until the entire needle 302 is destroyed) presents a great advantage as it prevents sparks from escaping. It also eliminates all risk of burning and incident by fire. Although the destroyer apparatus 100 may be used with a variety of electrical adapters or the like, as long as the battery 115 is charged normally, no external energy sources are required.

One advantage of the apparatus of the present invention over other methods is in transportability. The needle may be destroyed immediately after use anywhere. The risk of transport of sharp infected needles is eliminated.

It should be recognized that although this system has disclosed in terms of a particular shape and design, the syringe destroyer could be a variety of shapes and sizes and they would be within the spirit and scope of the present invention. In addition, the indicators utilized for indicating that the battery is charged, charging or ready for use can be a variety of types and their use would be within the spirit and scope of the present invention. Finally, a number of different types of circuits can be utilized to perform the functions of the circuit 200 and their use would be within the spirit and scope of the present invention.

Although the present invention has been described in accordance with the embodiments shown in the figures one of ordinary skill in the art will recognize there could be variations to those embodiments and those variations would be within the spirit and scope of the present invention. Accordingly, many modifications may be made by one of ordinary skill in the art without departing from the spirit and scope of the present invention, the scope of which is defined by the appended claims.

What is claimed is:

1. An apparatus for the destruction of a needle utilized in a syringe comprising:

a housing member;

a plate member coupled to the housing member; the plate member including an opening therethrough for receiving the needle;

a voltage source coupled to the plate member;

a switch means located on an external portion of the housing member for causing an electrical current to be applied to the plate member; and circuit means coupled to the voltage source and the plate member for melting the needle and sealing the syringe, the circuit means including a current generator coupled to the voltage source and a sensor means coupled to the switch means and the plate member, the sensor means for controlling the switch means such that the switch means will shut off the circuit means after a predetermined time period.

2. The apparatus of claim 1 in which the voltage source comprise a battery.

3. The apparatus of claim 1 which further includes:

a first light source located on an external portion of the housing member and coupled to the circuit means for indicating the voltage source is fully charged;

a second light source located on the external portion of the housing member and coupled to the circuit means for indicating the voltage source is not fully charged; and a third light source located on the external portion of the housing member and coupled to the circuit means for indicating that the voltage source has been recharged.

4. The apparatus of claim 1 which further includes:

a handle member coupled to the external portion of the housing member.

5. The apparatus of claim 1 which further includes:

a removable drawer member located in an interior portion of the housing member below the plate member for collecting a residue from the melting of the needle.

6. The apparatus of claim 1 in which the plate member includes a resilient means to allow the plate member to be movable when the needle is inserted.

7. The apparatus of claim 1 in which the plate member is located at an oblique angle within the housing member.

8. The apparatus of claim 6 in which the resilient means comprises a plurality of spring members.

9. An apparatus for the destruction of a needle utilized in a syringe comprising:

a housing member;

a handle member coupled to the external portion of the housing member;

a plate member coupled to the housing member; the plate member including an opening therethrough for receiving the needle, the plate member also including a resilient means for allowing the plate member to be movable when the needle is inserted through the opening;

a removable drawer member located in an interior portion of the housing member below the plate member for collecting a residue from the melting of the needle;

a voltage source coupled to the plate member, the voltage source comprise a battery;

circuit means coupled to the voltage source and the plate member for melting the needle and sealing the syringe, the circuit means including a current generator coupled to the voltage source and a sensor means coupled to the plate member;

a first light source located on an external portion of the housing member and coupled to the circuit means for indicating the voltage source is fully charged;

a second light source located on the external portion of the housing member and coupled to the circuit means for indicating the voltage source is not fully charged;

a third light source located on the external portion of the housing member and coupled to the circuit means for indicating that the voltage source has been recharged; and switch means located on an external portion of the housing member and coupled to the current generator and the sensor of the circuit means for causing an electrical current to be applied to the plate member, the sensor for controlling the switch means such that the switch means will shut off the circuit means after a predetermined time period.

10. The apparatus of claim 9 in which the plate member is located at an oblique angle within the housing member.

11. The apparatus of claim 9 in which the resilient means comprises a plurality of spring members.

* * * * *